US012285606B1

United States Patent
Choe et al.

(10) Patent No.: US 12,285,606 B1
(45) Date of Patent: Apr. 29, 2025

(54) COMPREHENSIVE SECOND-LANGUAGE ACQUISITION SYSTEM LEVERAGING SLEEP NEUROMODULATION AND NEUROAUGMENTED EXECUTIVE CONTROL

(71) Applicant: HRL Laboratories, LLC, Malibu, CA (US)

(72) Inventors: Jaehoon Choe, Agoura Hills, CA (US); Praveen K. Pilly, West Hills, CA (US)

(73) Assignee: HRL LABORATORIES, LLC, Malibu, CA (US)

( * ) Notice: Subject to any disclaimer, the term of this patent is extended or adjusted under 35 U.S.C. 154(b) by 393 days.

(21) Appl. No.: 17/675,944

(22) Filed: Feb. 18, 2022

Related U.S. Application Data

(60) Division of application No. 16/375,598, filed on Apr. 4, 2019, now Pat. No. 11,285,320, which is a
(Continued)

(51) Int. Cl.
*A61N 1/36* (2006.01)
*A61B 5/00* (2006.01)
(Continued)

(52) U.S. Cl.
CPC ............ *A61N 1/3603* (2017.08); *A61B 5/291* (2021.01); *A61B 5/4809* (2013.01);
(Continued)

(58) Field of Classification Search
CPC .... A61N 1/3603; A61N 1/0456; A61B 5/291; A61B 5/7475; A61B 5/4809; A61B 5/6814; G06F 9/542; G09B 19/06
See application file for complete search history.

(56) References Cited

U.S. PATENT DOCUMENTS

| 5,010,495 A | 4/1991 | Willetts |
|---|---|---|
| 6,435,876 B1 | 8/2002 | Chen |

(Continued)

FOREIGN PATENT DOCUMENTS

| EP | 2409641 | 1/2012 |
|---|---|---|
| WO | 2016-182947 | 11/2016 |

OTHER PUBLICATIONS

From U.S. Appl. No. 16/375,598 (now U.S. Pat. No. 11,285,320), Notice of Allowance mailed on Nov. 22, 2021.
(Continued)

*Primary Examiner* — Rex R Holmes
(74) *Attorney, Agent, or Firm* — Ladas & Parry, LLP

(57) ABSTRACT

A neuro-stimulation system having: a controller; a user interface arranged for, under control of the controller, providing a user with a series of information elements to be learned by the user; a non-invasive brain stimulator arranged for, under the control of the controller, tagging each information element of said series of information elements by stimulating a brain of the user with a different, unique, associated brain stimulus when the user is provided said information element by said user interface; and a non-invasive brain sensor arranged for sending to the controller data indicating a slow-wave sleep period of the user; wherein the controller is further arranged for cueing each information element of said series of information elements by causing the stimulator to stimulate the brain of the user with the brain stimuli associated with said series of information elements during said slow-wave sleep period of the user.

12 Claims, 6 Drawing Sheets

Related U.S. Application Data continuation-in-part of application No. 15/947,733, filed on Apr. 6, 2018, now Pat. No. 10,413,724.

(60) Provisional application No. 62/755,993, filed on Nov. 5, 2018.

(51) Int. Cl.
*A61B 5/291* (2021.01)
*A61N 1/04* (2006.01)
*G06F 9/54* (2006.01)
*G09B 19/06* (2006.01)

(52) U.S. Cl.
CPC .......... *A61B 5/6814* (2013.01); *A61B 5/7475* (2013.01); *A61N 1/0456* (2013.01); *G06F 9/542* (2013.01); *G09B 19/06* (2013.01)

(56) References Cited

U.S. PATENT DOCUMENTS

| | | |
|---|---|---|
| 6,751,505 B1 | 6/2004 | Van Den Honert |
| 7,052,277 B2 | 5/2006 | Kellman |
| 7,153,139 B2 | 12/2006 | Wen |
| 9,149,599 B2 | 10/2015 | Walter |
| 10,307,592 B1 | 6/2019 | Pilly |
| 10,413,724 B2 | 9/2019 | Choe |
| 11,285,320 B1 | 3/2022 | Choe |
| 2003/0225340 A1 | 12/2003 | Collura |
| 2006/0041242 A1 | 2/2006 | Stypulkowski |
| 2006/0073452 A1 | 4/2006 | Merzenich |
| 2006/0212090 A1 | 9/2006 | Lozano |
| 2007/0060974 A1 | 3/2007 | Lozano |
| 2007/0142874 A1* | 6/2007 | John ............ A61N 2/006 607/45 |
| 2007/0213786 A1 | 9/2007 | Sackellares |
| 2009/0099623 A1 | 4/2009 | Bentwich |
| 2011/0015469 A1* | 1/2011 | Walter ............ A61B 5/4809 600/27 |
| 2011/0118534 A1 | 5/2011 | Baror |
| 2011/0159467 A1 | 6/2011 | Peot |
| 2011/0288610 A1 | 11/2011 | Brocke |
| 2012/0184870 A1 | 7/2012 | Shaw |
| 2013/0011817 A1 | 1/2013 | Cohen Kadosh |
| 2013/0066392 A1 | 3/2013 | Simon |
| 2013/0225953 A1 | 8/2013 | Oliviero |
| 2013/0288223 A1 | 10/2013 | Watterson |
| 2013/0338738 A1 | 12/2013 | Garcia Molina |
| 2014/0038147 A1 | 2/2014 | Morrow |
| 2014/0257073 A1 | 9/2014 | Machon |
| 2014/0275926 A1 | 9/2014 | Scott |
| 2014/0288614 A1 | 9/2014 | Hagedorn |
| 2015/0050623 A1 | 2/2015 | Falash |
| 2015/0066104 A1 | 3/2015 | Wingeier |
| 2015/0079560 A1 | 3/2015 | Cowan |
| 2015/0105837 A1 | 4/2015 | Aguilar Domingo |
| 2015/0174418 A1 | 6/2015 | Tyler |
| 2015/0238762 A1 | 8/2015 | Pal |
| 2015/0294074 A1 | 10/2015 | Kawato |
| 2016/0206871 A1 | 7/2016 | Weisend |
| 2016/0256691 A1 | 9/2016 | Cecchi |
| 2017/0043167 A1 | 2/2017 | Widge |
| 2017/0113046 A1* | 4/2017 | Fried ............ A61N 1/36082 |
| 2017/0224990 A1 | 8/2017 | Goldwasser |
| 2017/0249853 A1 | 8/2017 | Weiss |
| 2017/0304623 A1 | 10/2017 | Tandon |
| 2017/0368348 A1 | 12/2017 | Le Van Quyen |
| 2018/0169411 A1 | 6/2018 | Goodall |
| 2018/0221644 A1 | 8/2018 | Grill |
| 2020/0139113 A1 | 5/2020 | Shin |

OTHER PUBLICATIONS

From U.S. Appl. No. 16/375,598 (now U.S. Pat. No. 11,285,320), Office Action mailed on Sep. 10, 2021.
From U.S. Appl. No. 16/375,598 (now U.S. Pat. No. 11,285,320), Office Action mailed on Apr. 21, 2021.
From U.S. Appl. No. 16/375,598 (now U.S. Pat. No. 11,285,320), Office Action mailed on Jan. 21, 2021.
From U.S. Appl. No. 16/375,593 (now U.S. Pat. No. 11,285,320), Notice of Allowance mailed on Nov. 23, 2021.
From U.S. Appl. No. 16/375,593 (now U.S. Pat. No. 11,285,320), Office Action mailed on Oct. 19, 2021.
From U.S. Appl. No. 16/375,593 (now U.S. Pat. No. 11,285,320), Office Action mailed on Aug. 19, 2021.
From U.S. Appl. No. 16/375,593 (now U.S. Pat. No. 11,285,320), Office Action mailed on Apr. 30, 2021.
Acheson, D. J., et al. "A common neural substrate for language production and verbal working memory," Journal of Cognitive Neuroscience, 23(6), pp. 1358-1367. (2011).
Anderson, J. R., "Cognitive skills and their acquisition," Psychology Press, pp. 143-146 and pp. 243-249,(1981). cited by applicant.
Apoorvagiri, N., "Mental Stress and its Implications on Reaction time," International Journal of Computer Trends and Technology, May 2013, pp. 1426 to 1430.
Bates, E., et al. "Functionalism and the competition model," The crosslinguistic study of sentence processing, 3, pp. 73-112. (1989), 60 pages.
Beckner, C., et al., "Language is a complex adaptive system: Position paper," Language Learning, 59(s1), 1-26 (2009).
Berenyii, A., et al. "Closed-loop control of epilepsy by transcranial electrical stimulation," Science, vol. 337(6095), 735-737, (2012).
Bikson, M., et al., "Neuroscience: transcranial devices are not playthings," Nature, vol. 501(7466), 167-167, (2013).
Brunoni, A. R., et al., "Clinical research with transcranial direct current stimulation (tDCS): challenges and future directions," Brain stimulation, 5(3), 175-195, (2012).
Buckner, R. L., "Memory and executive function in aging and AD: multiple factors that cause decline and reserve factors that compensate," Neuron, vol. 44(1), 195-208, 2004.
Carpenter, J. S., "Psychometric evaluation of the Pittsburgh sleep quality index," Journal of Psychosomatic Research, vol. 45, No. 1, pp. 5-13, 1998.
Choe, J., et al., "Transcranial direct current stimulation modulates neuronal activity and learning in pilot training," Frontiers in human neuroscience, vol. 10, (25 pages) (2016).
Christoff, Joseph A., "Foreign Languages: Human Capital Approach Needed to Correct Staffing & Proficiency Shortfalls," 2002, 56 pages.
Clark, V. P., et al. "TDCS guided using fMRI significantly accelerates learning to identify concealed objects," Neuroimage, 59(1), 117-128, (2012).
Cox, R., et al., "Sound asleep: processing and retention of slow oscillation phase-targeted stimuli," PLOS One, vol. 9, Issue 7, e101567. (2014), pp. 1-12.
Creutzfeldt O.D., et al., "Influence of transcortical d-c currents on cortical neuronal activity," Experimental Neurology, Jun. 1962; 5: pp. 436-452.
Dekeyser, R. M., "What makes learning second-language grammar difficult? A review of issues," Language learning, 55(S1), 1-25 (2005).
DeKeyser, R., "Beyond focus on form: Cognitive perspectives on learning and practicing second language grammar," Focus on form in classroom second language acquisition, 42-63 (1998).
Diekelmann S, et al., "Offline consolidation of memory varies with time in slow wave sleep and can be accelerated by cuing memory reactivations," Neurobiology Learn and Memory, Sep. 2012; 98(2): pp. 103-111.
Dijk, D. J., "Regulation and functional correlates of slow wave sleep," Journal of Clinical Sleep Medicine, vol. 5 (No. 2 Suppl), S6-S15, 2009.
Ferricci, R., et al., "Transcranial direct current stimulation improves recognition memory in Alzheimer disease," Neurology, 71(7), 493-498, (2008).
Floel, A., et al., "Noninvasive brain stimulation improves language learning," Journal of Cognitive Neuroscience, 20(8), 1415-1422, (2008).

(56) References Cited

OTHER PUBLICATIONS

Fregni, F., et al., "Anodal transcranial direct current stimulation of prefrontal cortex enhances working memory," Expeihuental brain research, 166(1), pp. 23-30, (2005).
Frohlich F, et al., "Endogenous electric fields may guide neocortical network activity," Neuron. Jul. 15, 2010; 67(1): pp. 129-143.
Gais, S, et al., "Low acetylcholine during slow-wave sleep is critical for declarative memory consolidation," Proceedings of National Academy of Sciences of USA, Feb. 17, 2004; 101(7); pp. 2140-2144.
Galvez-Garcia, G., et al. "Mitigating Simulator Adaptation Syndrome by means of tactile stimulation," Applied Ergonomics, 58, 13-17. (2017).
Gerrard, J. L., "Sequence reactivation in the hippocampus is impaired in aged rats," Journal of Neuroscience, 28(31), 7883-7890, 2008.
Hodges, S., "SenseCam: A wearable camera that stimulates and rehabilitates autobiographical memory," Memory, 19(7), 685-696, 2011 (18 pages).
Jacobson, L., et al. "tDCS polarity effects in motor and cognitive domains: a meta-analytical review," Experimental brain research, 216(1), 1-10, (2012).
Ji, D, et al., "Coordinated memory replay in the visual cortex and hippocampus during sleep," Nature Neuroscience. 2007, vol. 10(1): pp. 100-107.
Jutras MJ, et al., "Oscillatory activity in the monkey hippocampus during visual exploration and memory formation," Proceedings of National Academy of Sciences, Aug. 6, 2013, vol. 110, No. 32, pp. 13144-13149.
Kali S, et al., "Off-line replay maintains declarative memories in a model of hippocampal-neocortical interactions," Nature Neuroscience, 2004, vol. 7, No. 3, pp. 286-294.
Kirov R, et al., "Slow oscillation electrical brain stimulation during waking promotes EEG theta activity and memory encoding," Proceedings of National Academy of Sciences. 2009, vol. 106, pp. 15460-15465.
Krause, M. R., et al., "Transcranial Direct Current Stimulation Facilitates Associative Learning and Alters Functional Connectivity in the Primate Brain," Current Biology, 27(20), 3086-3096 (2017), 15 pages.
Lim, A. S., "Sleep fragmentation and the risk of incident Alzheimer's disease and cognitive decline in older persons," Sleep, vol. 36 No. 7, 1027-1032, 2013 (8 pages).
Little, S, et al. "Adaptive deep brain stimulation in advanced Parkinson disease," Annals of Neurology, 2013, 74:449-457.
Liu, M., et al., "A look at the research on computer-based technology use in second language learning: A review of the literature from 1990-2000," Journal of Research on Technology in Education, 34(3), 54 pages (2002).
Manenti, R., "Enhancing verbal episodic memory in older and young subjects after non-invasive brain stimulation," Frontiers in Aging Neuroscience, vol. 5, 2013 (9 pages).
Marshall, L., "Boosting slow oscillations during sleep potentiates memory," Nature, vol. 444(7119), pp. 610-613, 2006.
McNamara C.G., et al., "Dopaminergic neurons promote hippocampal reactivation and spatial memory persistence," Nature Neuroscience, 2014, vol. 17, No. 12 pp. 1658-1660.
Merzagora, Anna C., et al., "Prefrontal hemodynamic changes produced by anodal direct current stimulation." Neuroimage 49, No. 3 (2010): pp. 2304-2310.
Minichino, A., "Prefronto-cerebellar transcranial direct current stimulation improves sleep quality in euthymic bipolar patients: a brief report," Behavioural Neurology, 2014 (3 pages).

Mougeon, R., et al., "The sociolinguistic competence of immersion students," (vol. 47). Multilingual Matters, pp. 48-87, (2010).
Ngo, H., et al. "Driving Sleep Slow Oscillations by Auditory Closed-Loop Stimulation—A Self-Limiting Process," The Journal of Neuroscience, 35(17), 6630-6638. (2015).
Ngo, H., et al., "Auditory closed-loop stimulation of the sleep slow oscillation enhances memory," Neuron, 78(3), pp. 545-553 (2013).
Nitsche, M. A., et al., "Transcranial direct current stimulation: state of the art 2008," Brain stimulation, 1(3), 206-223, (2008).
Operation and Maintenance Overview, Fiscal Year 2016 Budget Estimates, Feb. 2015, Office of the Under Secretary of Defense (Comptroller) / Chief Financial Officer, p. 13. (282 pages).
Osipova D, et al., "Theta and gamma oscillations predict encoding and retrieval of declarative memory," Journal of Neuroscience, 2006; 26(28): pp. 7523-7531.
Osorio, I, et al. "Automated seizure abatement in humans using electrical stimulation," Ann Neurol 2005, 57:258-268.
Pace-Schott, E. F., "Age-related changes in the cognitive function of sleep," Progress in Brain Research, vol. 191, pp. 75-89, 2011.
Pienemann, Manfred (Editor), "Similarities and differences in L1 and L2 development. Opening up the perspective," by Gisela Hakansson, An introduction to processability theory. Crosslinguistic aspects of processability theory, 30, pp. 179-199. (2005).
Potowski, K., et al., "The effects of instruction on linguistic development in Spanish heritage language speakers," Language Learning, 59(3), 537-579, (2009).
Rasch B, et al., "Odor cues during slow-wave sleep prompt declarative memory consolidation," Science. 2007; 315(5817): pp. 1426-1429.
Rasch BH, et al., "Combined blockade of cholinergic receptors shifts the brain from stimulus encoding to memory consolidation," Journal of Cognitive Neuroscience, May 2006; 18(5): pp. 793-802.
Rolls E.T., "Hippocampo-cortical and cortico-cortical backprojections," Hippocampus. 2000; 10: pp. 380-388.
Rudoy J.D,, et al., "Strengthening Individual Memories by Reactivating Them During Sleep," Science. Nov. 20, 2009;326(5956): pp. 1079-1079.
Sachdev, P. S., "The prevalence of mild cognitive impairment in diverse geographical and ethnocultural regions: The COSMIC Collaboration," PLOS One, 10(11), e0142388, pp. 1-19, 2015.
Santostasi, G., et al., "Phase-locked loop for precisely timed acoustic stimulation during sleep," Journal of Neuroscience Methods, 259, 101-114, (2016).
Schade, C.M., et al., "Automatic adaptation of neurostimulation therapy in response to changes in patient position: results of the Posture Responsive Spinal Cord Stimulation (PRS) Research Study," Pain Physician 2011, 14:407-417.
Schultz, D.M., et al. "Sensor-driven position-adaptive spinal cord stimulation for chronic pain," Pain Physician 2012, 15:1-12.
Schumann, J. H., "Research on the acculturation model for second language acquisition," Journal of multilingual & multicultural development, 7(5), pp. 379-392. (1986).
Sederberg, P.B., et al., "Theta and gamma oscillations during encoding predict subsequent recall," Journal of Neuroscience, Nov. 26, 2003; 23(34): pp. 10809-10814.
Tergan, F., et al. "Low- frequency repetitive transcranial magnetic stimulation improves intractable epilepsy," The Lancet, vol. 353(9171), 2209. (1999).
Van Elmpt W.J., et al. "A model of heart rate changes to detect seizures in severe epilepsy," Seizure (2006), 15:366-375.

\* cited by examiner

COMPREHENSIVE SECOND-LANGUAGE ACQUISITION SYSTEM LEVERAGING SLEEP NEUROMODULATION AND NEUROAUGMENTED EXECUTIVE CONTROL

RELATED APPLICATIONS

This application is related to U.S. application Ser. No. 15/332,787, filed on Oct. 24, 2016, which is hereby incorporated by reference. This application is a division of U.S. patent application Ser. No. 16/375,598, filed on Apr. 4, 2019, which claims priority of U.S. application Ser. No. 15/947,733, filed on Apr. 6, 2018, which issued as U.S. Pat. No. 11,285,320 on Mar. 29, 2022, which is hereby incorporated by reference. This application claims priority of U.S. provisional application No. 62/755,993, filed on Nov. 5, 2018, the disclosures of which are hereby incorporated by reference.

STATEMENT REGARDING FEDERALLY SPONSORED RESEARCH OR DEVELOPMENT

This invention was made with Government support under contract number W911NF-16-C-0018 RAM DARPA RAM Replay. The Government has certain rights in the invention.

TECHNICAL FIELD

This presentation relates to a method and system for improving the teaching of materials to a user, for example the teaching of a second language.

BACKGROUND

While many neurophysiological aspects of language learning have been previously known, it was so far only possible to take advantage of such aspects indirectly through specific methods of behavioral training or playing back curriculum during the sleep state, which have not optimized learning as hoped. Adaptive learning programs, in which curricula are altered in situ in response to a real-time skill assessment, address some personalization aspects of training without contributing to the actual biological mechanisms of memory encoding and storage. Immersion programs and other efforts to encourage contemporaneous usage of Second Language, or SL, have shown to be of limited value, in which technical/formal SL learning increases while informal/casual speaking remain relegated to the mother language [see for example: Mougeon, R., Nadasdi, T., & Rehner, K. (2010): "*The sociolinguistic competence of immersion students*" (Vol. 47); Multilingual Matters].

Effective and time-efficient language learning is essential for students, foreign travelers, and in occupations that require multilingual fluency such as economists, international financial and intelligence analysts. The financial and man-hour cost to fluently train a second language is enormous. Typical estimates put language acquisition between 2-5 man-years of time.

The US Army spent $27 million on foreign language training through the Defense Language institute training facilities in 2001. Since then, an increase to programs of $287 million were attributed to an increase to Defense Language Institute Foreign Language Center (DFLIC) of 465 students in 2015. If these trends in language training needs continue, by 2029, the Army alone could save ~$30 million from a 1% increase in language training efficiency.

Demand for second language proficiency necessitates effective real-time assessments and novel training regiments to reduce time to mastery and providing increased skill acquisition & retention. This is estimated to cost $3.2 billion per year to the US aerospace industry alone.

Easing the learning of second language could also allow reducing Education-cost: +2200 classroom hrs. (L3 Proficiency, Cat. 4 Languages-State dept. FSI)

Immersion training of second languages (see for example: K. Potowski. "*The Effects of Instruction on Linguistic Development in Spanish Heritage Language Speakers.*" 2009) aims at improving overall fluency and voluntary/spontaneous use of the second language; in other words, training learners to use the Second Language (SL) naturalistically. The theoretical underpinnings of this method is rooted in executive monitoring and social cues; contemporary literature suggests that the tendency for language speakers to closely "monitor" their SL usage prevents natural speech patterns, leads to destructive interference between first and second languages, and stifles contemporaneous SL use [see for example DeKeyser, R. M. (2005). "*What makes learning second-language grammar difficult? A review of issues*". Language learning, 55 (S1), 1-25]. The social support present in a SL immersion environment is thought to reduce some of this excessive monitoring. However, social support is inconsistent and highly dependent on individual learning tendencies, and is difficult and resource-intensive to set up. Further, there is strong evidence that even young learners in an immersion course learn to "code-switch," using their mother tongue for actual informal communication while using the SL in structured, artificial, and formal contexts [see for example Potowski, K., Jegerski, J., & Morgan-Short, K. (2009). "*The effects of instruction on linguistic development in Spanish heritage language speakers*". Language Learning, 59 (3), 537-579].

Adaptive, data-driven training of second languages (see for example Liu, M., Moore, Z., Graham, L., & Lee, S. (2002). A look at the research on computer-based technology use in second language learning: A review of the literature from 1990-2000. Journal of Research on Technology in Education, 34 (3), 250-273.) has been tried, personalizing the process of second language learning by using adaptive curricula that change and adapt according to user performance and learning rates. More generalized versions of this concept of learning appear in items such as U.S. Pat. No. 7,052,277 B2 (System and Method for Adaptive Learning, 2006), and more specific instances exist in U.S. Pat. No. 5,010,495 A (Interactive language learning system, 1991). These methods, unfortunately do not work in the context of language learning, as SL acquisition seems to be a skill which in itself adapts to changing learning environmental conditions [see for example Beckner, C., Blythe, R., Bybee, J., Christiansen, M. H., Croft, W., Ellis, N. C., . . . & Schoenemann, T. (2009). "*Language is a complex adaptive system: Position paper*". Language learning, 59 (s1), 1-26.]. That is, any attempt to alter curriculums to match the ability of individual learners will be adapted to BY the learner, which may partially explain phenomena such as diglossia (using two languages for specific contexts), which impairs fluency. Further evidence for these techniques' failures lies in the actual landscape of commercial SL learning today: no current system utilizes an adaptive curriculum as laid out in the abovementioned patents, despite the fact that they have been approved for over 10 years. To this day, self-reported user motivation is the most reliable predictor in language learning paradigms.

There remains a need for an efficient system and method for improving the teaching of materials to a user; in particular for teaching a second language to a user.

SUMMARY

This disclosure relates to a novel training neuromodulatory intervention system/device that can for example be applied to second language (SL) training, and that allows enhanced encoding of learned material during waking periods and augmented consolidation of specific, critical information of interest during sleep periods. The device addresses crucial components of information acquisition process (for example the second language acquisition process) in a novel way, at the neurophysiological as well as the behavioral level in both initial acquisition periods and subsequent reinforcement periods. Additionally, the device/method can optionally address issues of excessive executive drive, found to prevent contemporaneous generation and usage of the SL augmenting the fluid transition between SL acquisition and SL use. Lastly, a novel device according to embodiments of this presentation can utilize a psychobehavioral model system that is used to selectively support knowledge/information that is insufficiently encoded or stored without affecting the naturalistic encoding/storage of other memories of interest. The modeling can also operate in combination with adaptive curricula, such that specific areas for improvement (e.g. subsets of a vocabulary list) are first identified, then incorporated into a behavioral model, which maximizes the augmentation of subskills of interest while minimally affecting the natural encoding of other subskills that, while important, may not require specific augmentation through neuromodulatory means.

A device or method according to an embodiment of this presentation can directly target the encoding and consolidation states of memory using transcranial direct current stimulation (tDCS) arranged in spatio-temporal, amplitude-modulated patterns (STAMP) in montages, which enhances directly the encoding of new information (e.g. new vocabulary, grammar) and aids in the consolidation of that information (long-term memory). Further, such device or method can also utilize tDCS neuromodulation to achieve disinhibition of language monitoring [see for example DeKeyser, R. (1998). "*Beyond focus on form: Cognitive perspectives on learning and practicing second language grammar. Focus on form in classroom second language acquisition*", 42-63.], which has been implicated in reduced SL use in everyday contexts and reduces the probability of gaining full fluency in SL learners. By applying tDCS during learning and (language) production, students/users will gain not only increase their proficiency in a specific SL but will also develop the general ability to increase acquisition and fluency in other SLs.

Embodiments of this presentation relate to a neuro-stimulation system having: a controller; a user interface arranged for, under control of the controller, providing a user with a series of information elements to be learned by the user; a non-invasive brain stimulator arranged for, under the control of the controller, tagging each information element of said series of information elements by stimulating a brain of the user with a different, unique, associated brain stimulus when the user is provided said information element by said user interface; and a non-invasive brain sensor arranged for sending to the controller data indicating a slow-wave sleep period of the user; wherein the controller is further arranged for cueing each information element of said series of information elements by causing the stimulator to stimulate the brain of the user with the brain stimuli associated with said series of information elements during said slow-wave sleep period of the user.

According to embodiments of this presentation, the controller is further arranged to cause the user interface to prompt the user to make use of each tagged information element; and the controller is further arranged to cause the non-invasive brain stimulator to stimulate a prefrontal cortex of the brain of the user while the user is prompted to make use of each tagged information element.

According to embodiments of this presentation, the non-invasive stimulator comprises transcranial direct current stimulation electrodes for applying small currents to a scalp and underlying brain structures of the user.

According to embodiments of this presentation, the series of information elements to be learned by the user comprises at least one of vocabulary lists, grammar rules, pronunciation exercises and prosody examples, in a foreign language to be learned by the user.

According to embodiments of this presentation, the controller is further arranged: to cause the user interface to prompt the user to make use of each tagged information element; to analyze a user reply to the user interface prompting to determine what tagged information elements need to be cued during a sleep of the user and what tagged information elements do not need to be cued during the sleep of the user; and to cue only the information element that need to be cued.

According to embodiments of this presentation, the controller is arranged to analyze the user reply to the user interface prompting to determine what tagged information element need to be cued and what tagged information element need not be cued by logging behavioral performance of the user.

According to embodiments of this presentation, the controller is arranged to analyze the user reply to the user interface prompting and to determine what tagged information element need to be cued and what tagged information element need not be cued by determining what information elements have not been learned properly by the user, and what information elements have been learned properly by the user.

Other embodiments of this presentation relate to a neuro-stimulation system comprising: a curriculum and stimulation scheduler arranged for associating to a unique brain stimulus each information element of a series of information elements to be learned by a user; a user sensory interface arranged for providing a user with said series of information elements; a user neural interface arranged for stimulating a brain of the user with the brain stimulus associated to each information element when said information element is provided to the user by said user sensory interface; wherein at least one of the user sensory interface and the user neural interface is provided for outputting respectively sensory data indicative of the user successfully learning said information elements and neural data indicative of the user successfully learning said information elements; the system further comprising a predictive model arranged for receiving at least one of said sensory and neural data, and for providing the curriculum and stimulation scheduler with data about an efficiency of each unique brain stimulus; the curriculum and stimulation scheduler being arranged for updating what brain stimulus is associated to what information element, said updating including associating a unique brain stimuli related to a successful learning of information elements to an information element poorly learned by the user.

According to embodiments of this presentation, the user sensory interface comprises at least one of a keyboard, a screen, a microphone and a speaker.

According to embodiments of this presentation, the user neural interface comprises a headgear having a plurality of electroencephalogram electrodes and a plurality of transcranial direct current stimulation electrodes.

According to embodiments of this presentation, each unique brain stimulus comprises a spatio-temporal, amplitude-modulated pattern of neural stimulation electrical signals.

According to embodiments of this presentation, the user neural interface is arranged to sense data indicative of a slow-wave sleep period of the user; and the user neural interface is arranged to stimulate a brain of the user with the brain stimuli associated with said series of information elements during said slow-wave sleep period of the user.

Other embodiments of this presentation relate to a neurostimulation method comprising: with a user interface, providing a user with a series of information elements to be learned by the user; with a non-invasive brain stimulator, tagging each information element of said series of information elements by stimulating a brain of the user with a different, unique, associated brain stimulus when the user is provided said information element by said user interface; with a non-invasive brain sensor, detecting a slow-wave sleep period of the user; and cueing each information element of said series of information elements by causing the stimulator to stimulate the brain of the user with the brain stimuli associated with said series of information elements during said slow-wave sleep period of the user.

According to embodiments of this presentation, the method further comprises: with the user interface, prompting the user to make use of each tagged information element; and with the non-invasive brain stimulator, stimulating a prefrontal cortex of the brain of the user while the user is prompted to make use of each tagged information element.

According to embodiments of this presentation, said stimulating the brain of the user with the non-invasive stimulator comprises applying small currents to the scalp and underlying brain structures of the user with transcranial direct current stimulation electrodes.

According to embodiments of this presentation, the series of information elements to be learned by the user comprises at least one of vocabulary lists, grammar rules, pronunciation exercises, and prosody examples, in a foreign language to be learned by the user.

According to embodiments of this presentation, the method further comprises: with the user interface: prompting the user to make use of each tagged information element; and further comprises: determining what tagged information element need to be cued during a sleep of the user and what tagged information element need not be cued during the sleep of the user; and cueing only the information element that need to be cued.

According to embodiments of this presentation, the method further comprises: with the user interface, determining what tagged information element need to be cued and what tagged information element need not be cued by logging behavioral performance of the user.

According to embodiments of this presentation, the method further comprises: with the user interface, determining what tagged information element need to be cued and what tagged information element need not be cued by determining what information elements have not been learned properly by the user, and what information elements have been learned properly by the user.

Other embodiments of this presentation relate to a neurostimulation method comprising: with a curriculum and stimulation scheduler, associating each information element of a series of information elements to be learned by a user to a unique brain stimulus; with a user sensory interface, providing the user with said series of information elements; with a user neural interface, stimulating a brain of the user with the brain stimulus associated to each information element when said information element is provided to the user by said user sensory interface; with at least one of the user sensory interface and the user neural interface, outputting respectively sensory data indicative of the user successfully learning said information elements and neural data indicative of the user successfully learning said information elements; with a predictive model, receiving at least one of said sensory and neural data, and providing the curriculum and stimulation scheduler with data about the efficiency of each unique brain stimulus; and with the curriculum and stimulation scheduler, updating what brain stimulus is associated to what information element, said updating including associating a unique brain stimuli related to a successful learning of information elements to an information element poorly learned by the user.

According to embodiments of this presentation, the method further comprises using a user sensory interface having at least one of a keyboard, a screen, a microphone and a speaker.

According to embodiments of this presentation, the method further comprises using a user neural interface having a headgear with a plurality of electroencephalogram electrodes and a plurality of transcranial direct current stimulation electrodes.

According to embodiments of this presentation, each unique brain stimulus comprises a spatio-temporal, amplitude-modulated pattern of neural stimulation electrical signals.

According to embodiments of this presentation, the method further comprises, with the user neural interface, sensing data indicative of a slow-wave sleep period of the user; and with the user neural interface, stimulating the brain of the user with the brain stimuli associated with said series of information elements during said slow-wave sleep period of the user.

DESCRIPTION

Figure 1:
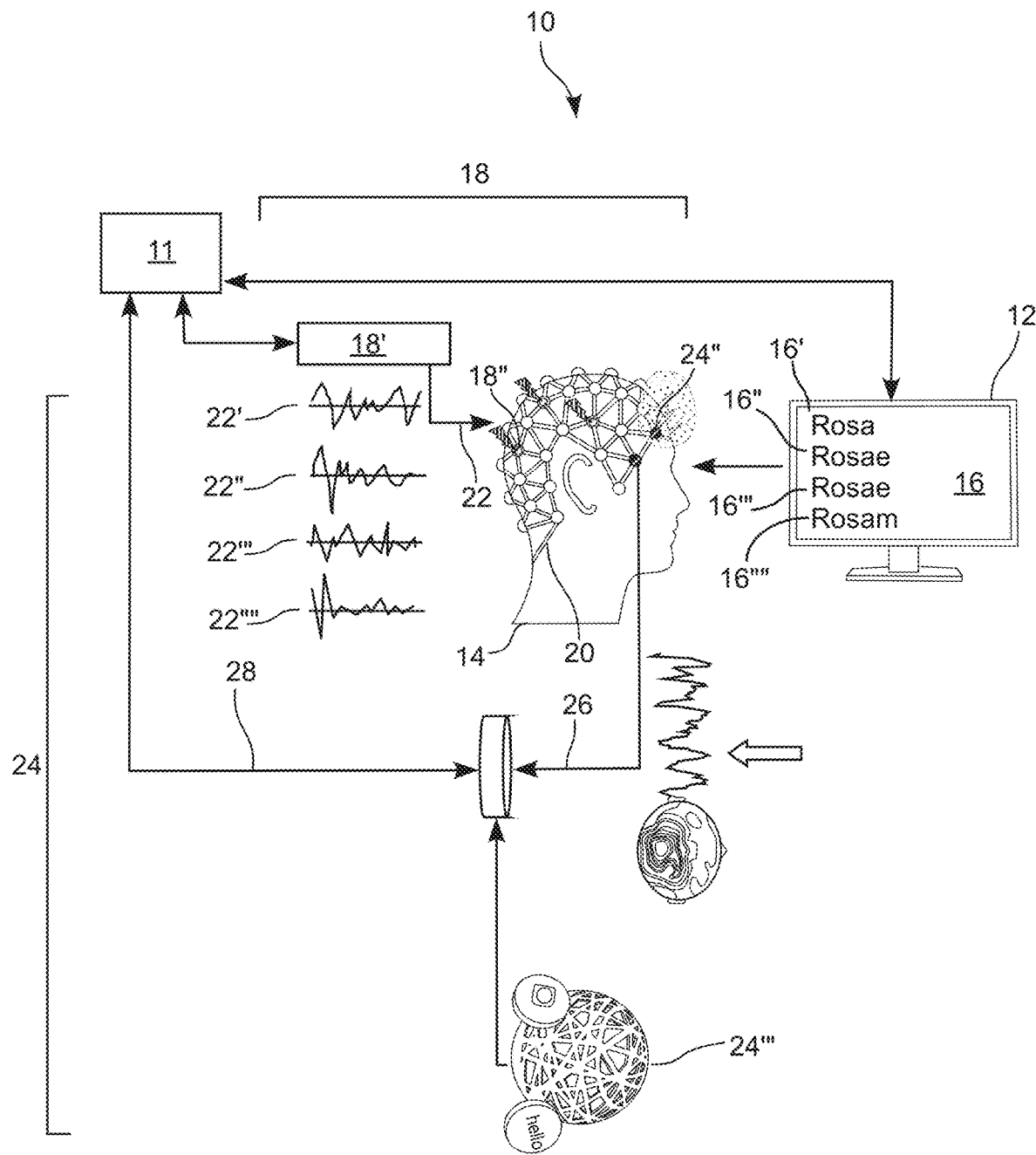
FIG. 1 illustrates a neuro stimulation system according to embodiments of this presentation.

The following description is presented to enable one of ordinary skill in the art to make and use the teachings of this presentation and to incorporate them in the context of particular applications. Various modifications, as well as a variety of uses in different applications will be readily apparent to those skilled in the art, and the general principles defined herein may be applied to a wide range of embodiments. Thus, the present invention is not intended to be limited to the embodiments presented, but is to be accorded the widest scope consistent with the principles and novel features disclosed herein.

In the following detailed description, numerous specific details are set forth in order to provide a more thorough understanding of embodiments of this presentation. However, it will be apparent to one skilled in the art that such embodiments may be practiced without necessarily being limited to these specific details.

All the features disclosed in this presentation, (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

A device or method according to embodiments of this presentation represent a very wide shift in second language acquisition (SLA), in that it targets neurophysiological (i.e. biological) mechanisms of learning rather than attempting to tailor the curriculum or adapting the learning paradigm to individual learning styles. Further, a device or method according to embodiments of this presentation is novel at least in that it uses a technological intervention to encourage spontaneous usage of SL rather than encouragement through secondary means such as social pressure or environmental context. The neuromodulatory approach is direly needed in a field which has not seen significant advancement in training in over 2 decades, despite many paradigms techniques existing as prior art. Perhaps for reasons of efficacy or real-world practicability, such techniques have not been utilized in modern language training programs.

In the past, the technology used by the claimed invention was not used and it was unclear 1) whether the technology could be used to target specific memories (in this context, study material that requires an augmentative boost) and 2) whether the technology was feasibly usable in rapid, real-world practicable fashion. These concerns were addressed through research at HRL, which comprise U.S. application Ser. No. 15/332,787, which is hereby incorporated by reference, and U.S. application Ser. No. 15/947,733; which is hereby incorporated by reference.

A goal of embodiments of this presentation is to rapidly accelerate the acquisition of second language acquisition (SLA) using neurostimulation. Prior work from HRL [see for example Choe, J., Coffman, B. A., Bergstedt, D. T., Ziegler, M. D., & Phillips, M. E. (2016). "*Transcranial direct current stimulation modulates neuronal activity and learning in pilot training*". Frontiers in human neuroscience, 10; see also Krause, M. R., Zanos, T. P., Csorba, B. A., Pilly, P. K., Choe, J., Phillips, M. E., . . . & Pack, C. C. (2017). "*Transcranial Direct Current Stimulation Facilitates Associative Learning and Alters Functional Connectivity in the Primate Brain*". Current Biology, 27 (20), 3086-3096.] and others [see for example Floel, A., Rösser, N., Michka, O., Knecht, S., & Breitenstein, C. (2008). "*Noninvasive brain stimulation improves language learning*". Journal of Cognitive Neuroscience, 20 (8), 1415-1422] have demonstrated that it is possible to enhance the learning of complex, real-world skills (33% more consistent) and novel lexicons (up to 40% faster) using transcranial Direct Current Stimulation (tDCS) targeted to frontal brain regions. Further, current research involving memory replays (U.S. Ser. No. 15/332,787), show that by applying a specific pattern of neurostimulation (STAMP) concomitant with a memory of interest, one can enhance the consolidation of that memory during sleep by cueing the same STAMP at specific sleep phases in closed-loop fashion (U.S. Ser. No. 15/947,733). These new findings enable direct augmentation of memory storage and retrieval processes and are the key to aiding the memorization and internalization of many critical components of SLA, including vocabulary, grammar, and semantic acquisition and retention.

According to embodiments of this presentation, disinhibiting language monitoring during learning and production allows students to not only gain increased proficiency in a specific SL but also develop the general ability to increase acquisition and fluency by decreasing the monitoring tendency of executive control and increasing the extemporaneous use of SL that marks true nativity and fluency. Embodiments of this presentation comprise a machine-aided learning system or method, that leverages existing experience with sleep (DARPA RAM Replay) and provides behavioral learning enhancement that modulates top-down executive inhibition (dlPFC dis/inhibition using tDCS), control error-monitoring behavior, and constructive interference during progressive learning of SLs. This method coupled with the memory-encoding and consolidation enhancement described above can operate together with a smartphone or computer-based learning approach, that automatically applies appropriate STAMP-based tagging information as a user learns vocabulary or grammar rules. Further, data can be collected throughout the learning session in order to learn which subsets of vocabulary, grammar, or other fundamentals of SL need augmentation, in order to apply tagging and cueing information only to those aspects of the curriculum that require neuromodulative support. During recitation, or other similar oral or lexical usage scenarios, non-specific pre-frontal tDCS stimulation can optionally be applied in order to reduce the drive of executive control and encourage the fluidic use of language. After the direct language training period, the user can wear a neurostimulation device (e.g. a cap or headband wearable containing EEG recording electrodes and tDCS stimulation electrodes) such that a closed-loop, STAMP-based neuromodulation intervention may be applied during Slow-Wave Oscillation (SWO) sleep, in order to cue previously tagged item for increased likelihood of consolidation and retention. The combination of the above features results in increased assimilation and incorporation of SL vocabulary and grammar rules, and also decreases the effort thresholds required to spontaneously utilize the SL in everyday speech. This overcomes the two primary stumbling blocks to SLA in modern theories of SL learning.

FIG. 1 illustrates a neuro stimulation system 10 according to embodiments of this presentation, which comprises a controller 11 and a user interface 12 arranged for, under the control of controller 11, providing a user 14 with a series 16 of information elements (16', 16", 16''' and 16'''' illustrated) to be learned by the user 14. Such information elements can comprise one or more of vocabulary lists, grammar rules, pronunciation exercises and prosody examples, for example in a foreign language to be learned by the user. According to an embodiment of this presentation, system 10 also comprises a non-invasive brain stimulator 18, having for example a signal processor 18' and stimulator electrodes 18" arranged on a headgear 20 (the electrodes 18" can for example be transcranial direct current stimulation electrodes for applying small currents to the scalp and underlying brain structures of the user 14). According to embodiments of this presentation, the stimulator 18 is arranged for, under the control of controller 11, tagging each information element (16', 16", 16''' and 16'''') of said series 16 of information elements. According to an embodiment of this presentation, the tagging comprises stimulating the brain of the user with a different, unique, associated brain stimulus 22 (22', 22", 22''' and 22'''' illustrated) at the same time when the user 14 is provided said information element by user interface 12. According to an embodiment of this presentation, system 10 also comprises a non-invasive brain sensor 24 arranged for sending to controller 11 data 26 indicating a slow-wave sleep period of the user 14. According to an embodiment of this presentation, non-invasive brain sensor 24 can comprise a signal processor 24' coupled to sensing electrodes 24", the electrodes arranged for example on headgear 20 in alternancy with stimulator electrodes 18". According to an embodiment of this presentation, non-invasive brain sensor 24 can be coupled to a further user sensor 24'''' also arranged for detecting data indicating a slow wave sleep period of the user. For example, further user sensor 24'''' can be arranged for capturing the breathing sounds of user 14.

According to an embodiment of this presentation, controller 11 is arranged for cueing each information element of said series 16 of information elements by causing 28 the stimulator 18 to stimulate the brain of the user 14 with the brain stimuli 22 associated with the series 16 of information elements during the slow-wave sleep period of the user.

As detailed hereafter, user interface 12 can be arranged for prompting user 14 to make use of each information element (16', 16", 16''', 16'''') that has been tagged; and the non-invasive brain stimulator 18 can be arranged for stimulating the prefrontal cortex of the user 14 while the user is prompted to make use of each tagged information element.

Figure 2:
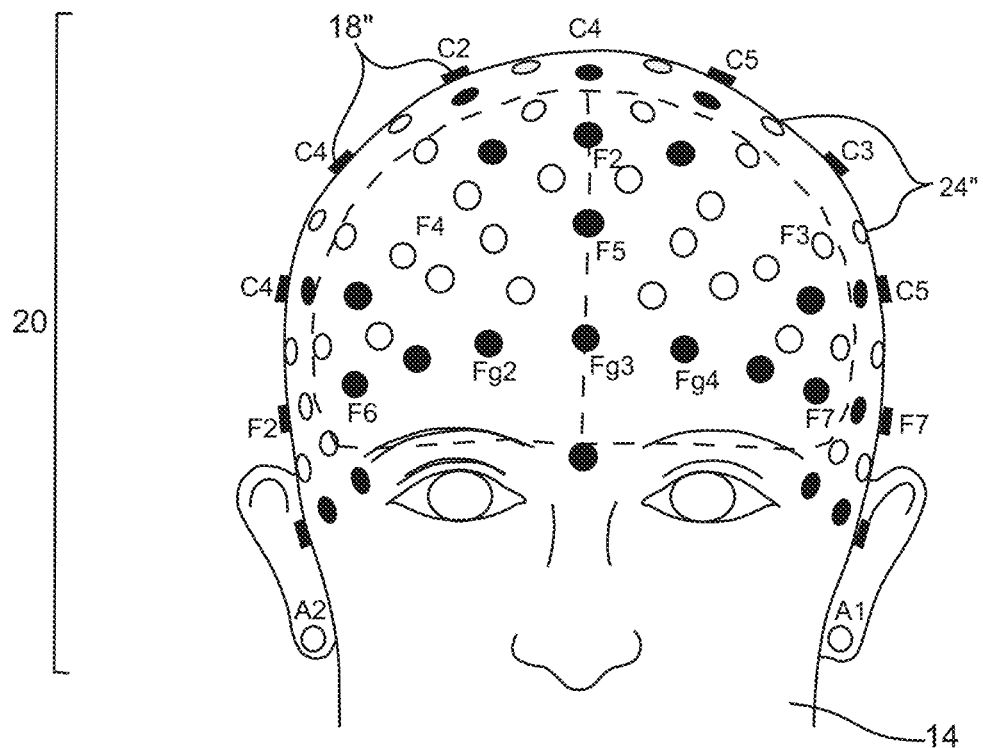
FIG. 2 illustrates details of a neuro stimulation system according to embodiments of this presentation.

FIG. 2 illustrates a headgear 20 according to embodiments of this presentation, which can comprise a wearable headcap, headband, helmet, or headwear that provides a mounting solution for the sensing electrodes 24" (which can be EEG electrodes) for monitoring brain signals and the stimulator electrodes 18" (which can be tDCS stimulation electrodes for applying small currents to the scalp and underlying brain structures, for example forming STAMPs. In previous research, one has utilized 32-channel EEG electrode arrays [see for example Choe, J., Coffman, B. A., Bergstedt, D. T., Ziegler, M. D., & Phillips, M. E. (2016). "*Transcranial direct current stimulation modulates neuronal activity and learning in pilot training*". Frontiers in human neuroscience, 10.] to 64-channel EEG electrode arrays, but sufficient spatio-temporal resolution was achieved for closed-loop stimulus with as few as 4-channels of electrode monitoring. According to an embodiment of this presentation, the number of stimulation (for example tDCS) channels used can be variable, to allow maximizing the library of unique STAMPs.

The Inventors have shown that up to 32-channels of tDCS stimulation electrodes can be used to generate libraries of 256 unique STAMPs. The Inventors have also shown that the greater the number of unique STAMPs, the greater the granularity of the tag-and-cue paradigm to enhance encoding and consolidation of specific memories; that is, an increased number of STAMP montages allows enhancing an increasingly specific and numerous set of memories/information of interest.

Figure 3:
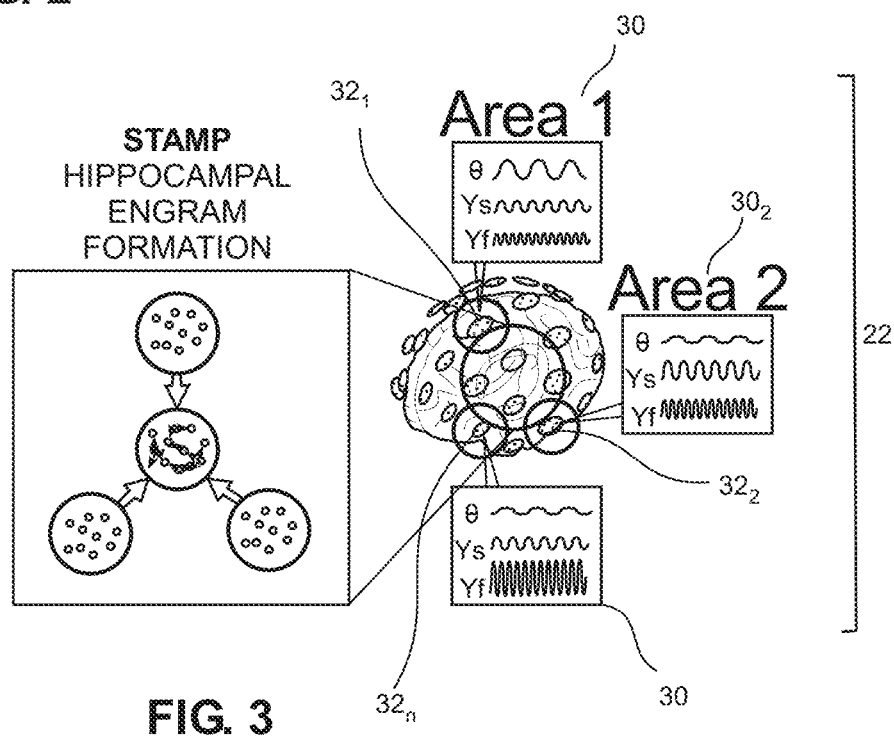
FIG. 3 illustrates the operation of a neuro stimulation system according to embodiments of this presentation.

FIG. 3 illustrates how neuromodulation can be achieved through tDCS and STAMP. A Neurostimulation device such as illustrated in FIG. 2 enables EEG-based brain signal monitoring as well as tDCS stimulation, both for generalized pre-frontal cortex stimulation and STAMP-based tagging and cueing. A memory acquired while receiving a predetermined STAMP stimulation can be preferentially evoked by applying the same STAMP stimulation at some critical point in the memory consolidation process, such as during SWO sleep (see U.S. application Ser. No. 15/332,787 and U.S. application Ser. No. 15/947,733). FIG. 3 shows a conceptual depiction of a STAMP-based tagging/cueing according to embodiments of this presentation: a unique STAMP stimulus applied during memory engram formation associates the STAMP pattern functionally with the stored memory. As illustrated, a unique STAMP stimulus 22 can comprise a plurality of different local stimuli $30i$, with $i=[1, n]$ that are emited each by a different stimulator electrode 18" toward a different area $32i$, with $i=[1, n]$ of the brain of user 14 under said electrode (where θ, Ys and Yf in the figure correspond to endogenous brain oscillations of different frequencies (theta: θ; slow gamma: Ys; fast gamma: Yf)]

A SL teaching device, or neuro-stimulation system, according to embodiments of this presentation and such as illustrated in FIG. 1, comprises two primary functions linked with neurostimulative intervention, as follows:

A first function is the association of discrete instructional items with unique STAMP montages, the instructional items including (but not being limited to) vocabulary lists, grammar rules, pronunciation exercises and prosody examples. The STAMPs or STAMP montages can be selected manually, but are preferably selected automatically by software. Each STAMP montage can be fed to the Neurostimulation device (brain stimulator), such that unique STAMPs 22 are applied as current across the channels of the neurostimulation cap 20 concomitant with the information 16 intended to be augmented or tagged. The "tagged" information can then be "cued" during the sleep memory consolidation phase to enhance its storage, and ultimately its retrieval.

According to an alternative embodiment, should a large quantity of unique STAMPs be readily available (for example in case the neurostimulation device has a plurality of channels and enables the generation of a very large STAMP library), every piece of information presented by a neuro-stimulation system according to an embodiment of this presentation may be initially tagged. Then, based on evaluations, only a subset of the tagged pieces of information can be cued in order to support only certain information of interest. An example of a piece of information of interest may be a central grammar rule, from which a great many linguistic concepts are linked, or a particularly difficult piece of vocabulary, which the user is struggling to learn. Through this tag-and-cue method, an embodiment of this presentation uses neuromodulatory intervention to boost learning of specific memories, thus improving memorization and retention of SL components using what is otherwise a "standard" adaptive curriculum.

According to an embodiment of this presentation, a second function/neurostimulation component of the neurostimulation system comprises a recitation function (similar to the ones of many contemporary programs, such as those known under the commercial names of Rosetta or Duolingo) that prompts SL learners to utilize their current learned skills to vocalize the second language. Vocalizing has been shown by research to be hampered by executive monitoring behavior (i.e. "looking for and dreading errors") which leads to reduced fluency and motivation, both key aspects of SLA. This executive control may be reduced by a generalized stimulation of the pre-frontal cortex of the brain, which has previously been shown to reduce overcorrection behaviors and increase brain signals associated with engagement in general skill-learning paradigms [see for example Choe, J., Coffman, B. A., Bergstedt, D. T., Ziegler, M. D., & Phillips, M. E. (2016). "*Transcranial direct current stimulation modulates neuronal activity and learning in pilot training*". Frontiers in human neuroscience, 10; see also Krause, M. R., Zanos, T. P., Csorba, B. A., Pilly, P. K., Choe, J., Phillips, M. E., . . . & Pack, C. C. (2017). "*Transcranial Direct Current Stimulation Facilitates Associative Learning and Alters Functional Connectivity in the Primate Brain*". Current Biology, 27 (20), 3086-3096]. Leveraging this property of neuromodulation, a neuro-stimulation system according to embodiments of this presentation can engage a pre-frontally-targeted tDCS montage during the recitation/extemporaneous language construction phase of the curriculum, thus reducing the tendency to overcorrect and encourage fluid use of the SL.

Figures 4A, 4B, 4C:
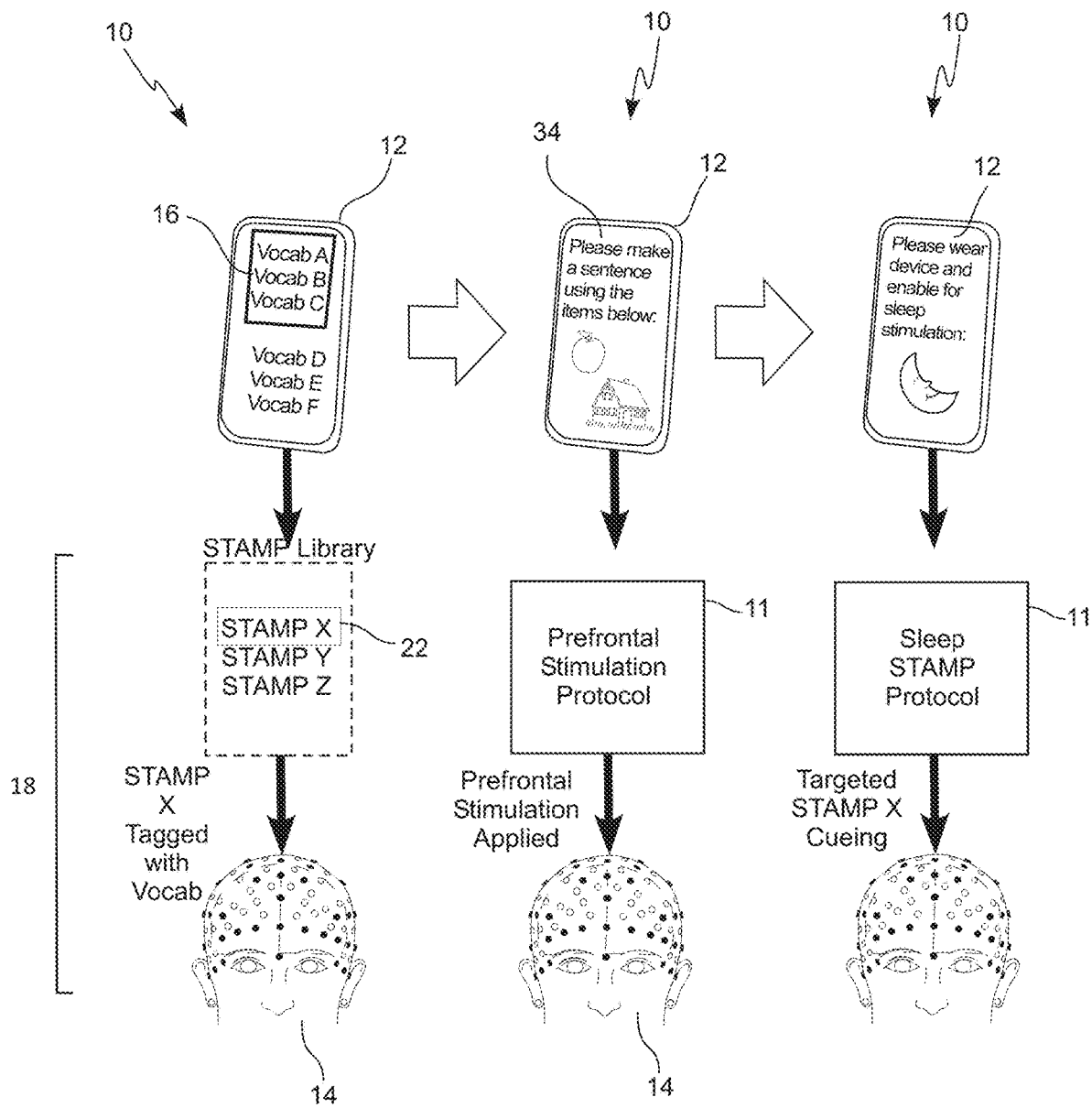
FIGS. 4A, 4B and 4C illustrate the operation of a neuro stimulation system according to embodiments of this presentation.

FIG. 4A illustrates the operation of a neuro-stimulation system according to an embodiment of this presentation, where user interface 12 provides user 14 with a series 16 of information elements to be learned by the user; and wherein stimulator 18 tags each information element of said series 16 of information elements by stimulating the brain of the user with a different, unique, associated brain stimulus 22 when user 14 is provided said information element by user interface 12. According to an embodiment, the user interface 12 can be part of a mobile computer and the controller 11 can be implemented by a software program running on the mobile computer. In such embodiment, the operation shown in FIG. 4A can be achieved by having the mobile computer software identify a SL curriculum item 16 to be augmented/tagged and automatically select a STAMP 22 from a STAMP library. The mobile computer software can then interface with the neurostimulation hardware/headgear 20 (bearing the stimulator electrodes 18") to apply the selected STAMP as the user experiences the curriculum item 16 in question.

FIG. 4B illustrates the operation of a neuro-stimulation system 10 according to an embodiment of this presentation, where user interface 12 is further arranged for prompting 34 the user to make use of each tagged information element; and the non-invasive brain stimulator 18 is arranged for, under the control of controller 11, stimulating the prefrontal cortex of user 14 (for example using appropriately located tDCS) while user 14 is prompted to make use of each tagged information element 16. For example, user 14 can be asked to compose a statement out loud in the SL using non-lexical cues, and the controller 11 can then automatically attempt to cause stimulator 18 to apply pre-frontal stimulation to increase the extemporary/fluidic nature of speech generation in SL.

FIG. 4C illustrates the operation of a neuro-stimulation system 10 according to an embodiment of this presentation, where after user interface 12 {optionally} instructs user 14 to wear the stimulator 18 during sleep, non-invasive brain sensor 24 sends (as shown in FIG. 1) to controller 11 data 26 indicating a slow-wave sleep period of user 14, and controller 11 cues each information element of said series 16 of information elements by causing the stimulator 18 to stimulate the brain of user 14 with the brain stimuli 22 associated with said series 16 of information elements during said slow-wave sleep period of user 14. In the embodiment outlined above where user interface 12 is part of a mobile computer and controller 11 is implemented by a software program running on the mobile computer, stimulator 18 has under the control of controller 11 a sleep function in which the STAMP stimuli applied in FIG. 4A are cued in closed loop fashion during the night during SWO sleep (see U.S. application Ser. No. 15/947,733 for detailed description of closed-loop system). In this way both fluidic SL production and memory encoding/consolidation of specific SL items are enhanced.

According to an embodiment of this presentation, when controller 11 causes the user interface to make user 14 use each tagged information element 16, as illustrated in FIG. 4B, controller 11 can be arranged to analyze the reply of user 14 to the user interface promptings, and to determine if there exist tagged information elements 16 that need to be cued during the sleep of the user, as opposed to tagged information element that need not be cued during the sleep of the user. This determination can be made by logging a behavioral performance of the user. For example, a tagged information element that needs to be cued can be an information element that has not been learned properly by the user.

Figure 5:
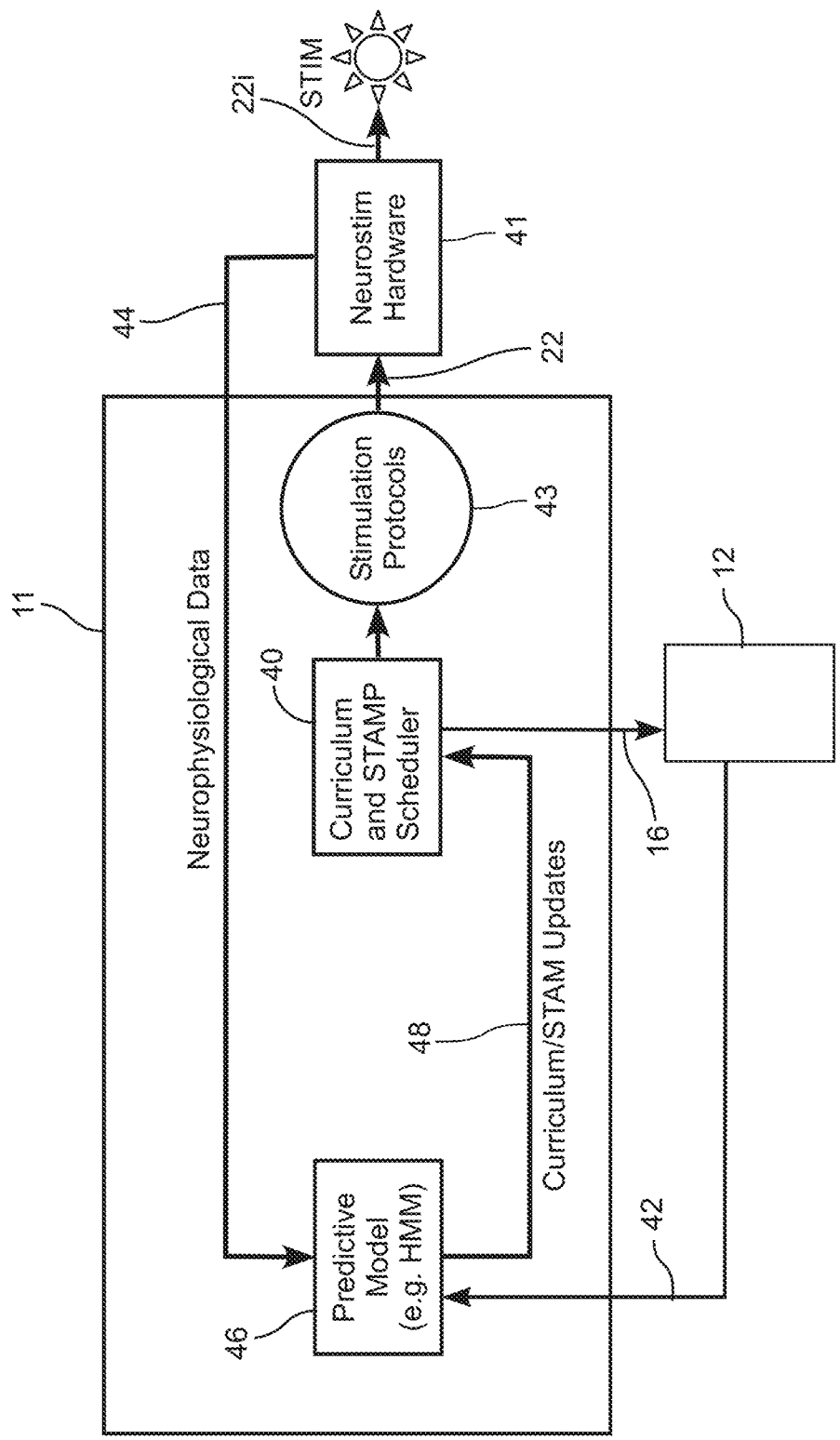
FIG. 5 illustrates a neuro stimulation system according to embodiments of this presentation.

FIG. 5 illustrates an embodiment of a neuro stimulation system according to this presentation, detailing controller 11. According to an embodiment, controller 11 comprises: a curriculum and stimulation scheduler 40 arranged for associating to a unique brain stimulus $22i$ each information element $16i$ of a series 16 of information elements to be learned by a user 14 (with i=1 to n, n being a number of informations to be learned by the user). According to an embodiment of this presentation, controller 11 is arranged to communicate with user sensory interface 12, which is arranged for providing user 14 with said series 16 of information elements. According to an embodiment of this presentation, controller 11 is also arranged to communicate with a user neural interface/neurostim hardware 41 (including brain stimulator 18, brain sensor 24 and headgear 20), arranged for stimulating the brain of user 14 with the brain stimulus $22i$ associated to each information element $16i$ at the time said information element $16i$ is provided to user 14 by user interface 12. A layer 43 of stimulation protocols can be used to translate instructions from the curriculum and stimulation scheduler 40 into the brain stimuli $22i$.

According to an embodiment of this presentation, the user sensory interface 12 can be provided for sending back to controller 11 sensory data 42 indicative of the user successfully learning said information elements (e.g. interface 12 can be arranged to record the way user 14 pronounces information elements $16i$ if the latter are vocabulary words). According to an embodiment of this presentation, user neural interface 41 can be provided to send back to controller 11 neural/neurophysiological data 44 indicative of the user successfully learning information elements $16i$ (e.g. electroencephalogram signals found to relate to the user successfully learning the elements).

According to an embodiment of this presentation, controller 11 further comprises a predictive model 46 arranged for receiving at least one of said sensory data 42 and neural data 44, and for providing the curriculum and stimulation scheduler 40 with data 48 about the efficiency of each unique brain stimulus; the curriculum and stimulation scheduler 40 being arranged for memorizing (as "efficient" brain stimuli) the brain stimuli that are related to the successful learning of information elements. According to embodiments of this presentation, controller 11 is arranged for updating what brain stimulus is associated to what information element, said updating including associating memorized efficient brain stimuli to information elements poorly learned by the user (e.g. not learned as well as other similar or comparable information elements).

According to an embodiment of this presentation, user sensory interface 12 comprises at least one of a screen and a speaker, and one of a microphone, a mouse, a touchscreen and a keyboard.

According to an embodiment of this presentation, controller 11 can continually log the behavioral performance of the user 14 (for example through pop-quiz-style testing and mini-evaluations) in order to determine which items of the curriculum require the most support. Initially, this may be achieved through a simple assessment-response feedback program that simply weighs and schedules tag-and-cue stimulation for items in which user 14 is performing poorly. However, a system according to this presentation is not limited to such simple assessments and may be developed such that intricacies of the language (structure, grammar, semantics) may be incorporated in order to predict performance in various areas (e.g., plural self-pronoun use in East-Asian languages may cause problems for speakers of singular self-pronoun languages such as English).

Predictions of user performance may be collected and modeled using processes similar, but not limited to, Hidden Markov Models (HMM), recursive neural networks (RNN), convolutional neural networks (CNN), and other machine learning strategies. Accurate predictions of user behavior can enable greater accuracy and targeting neuromodulatory intervention for increasingly specific items and content for both tag-and-cue and executive control contexts. While similar to "adaptive learning" concepts of the past, machine-learning for curriculum/intervention adjustment is much more efficacious due to the fact that the altered curriculum and neuromodulation directly address biologically relevant mechanisms of memory storage and retrieval.

Centrally, the curriculum and stimulation scheduler 40 (Curriculum and STAMP Scheduler) administers SLA exercises, sends STAMPs to the Neurostimulation hardware 41 for tag-and-cue purposes, and provides SLA learner performance data to the behavioral performance predictor 46 (here, represented as a Predictive Model driven by HMM, as an example). The prediction model can use input data including, but not limited to, neurophysiological data taken from EEG sensors and user performance data and can output 1) Changes to the SLA curriculum (e.g. course material) and 2) Reassignments of STAMP selection (i.e. identifies new items to be augmented). This predictive system is provided to increase in sophistication as the knowledge of SLA increases using this setup.

Neurostimulation, as applied to a tag-and-cue STAMP system, directly addresses the neurophysiological memory encoding aspect of learning, which bypasses individual learning styles, and directly targets the biological mechanisms for the storage and recollection of facts. This eliminates the risk that a user "out-adapts" an adaptive learning paradigm, and addresses the difficulty of learning new information without relying on user compliance and motivation. Application of this technology in more general fields indicates improvements in memory performance up to 50% over non-intervention control populations. Use of neuromodulatory enhancement of memory encoding and recall has great potential for improving training of SL by bypassing many of the issues inherent to complex skill acquisition.

Figure 6:
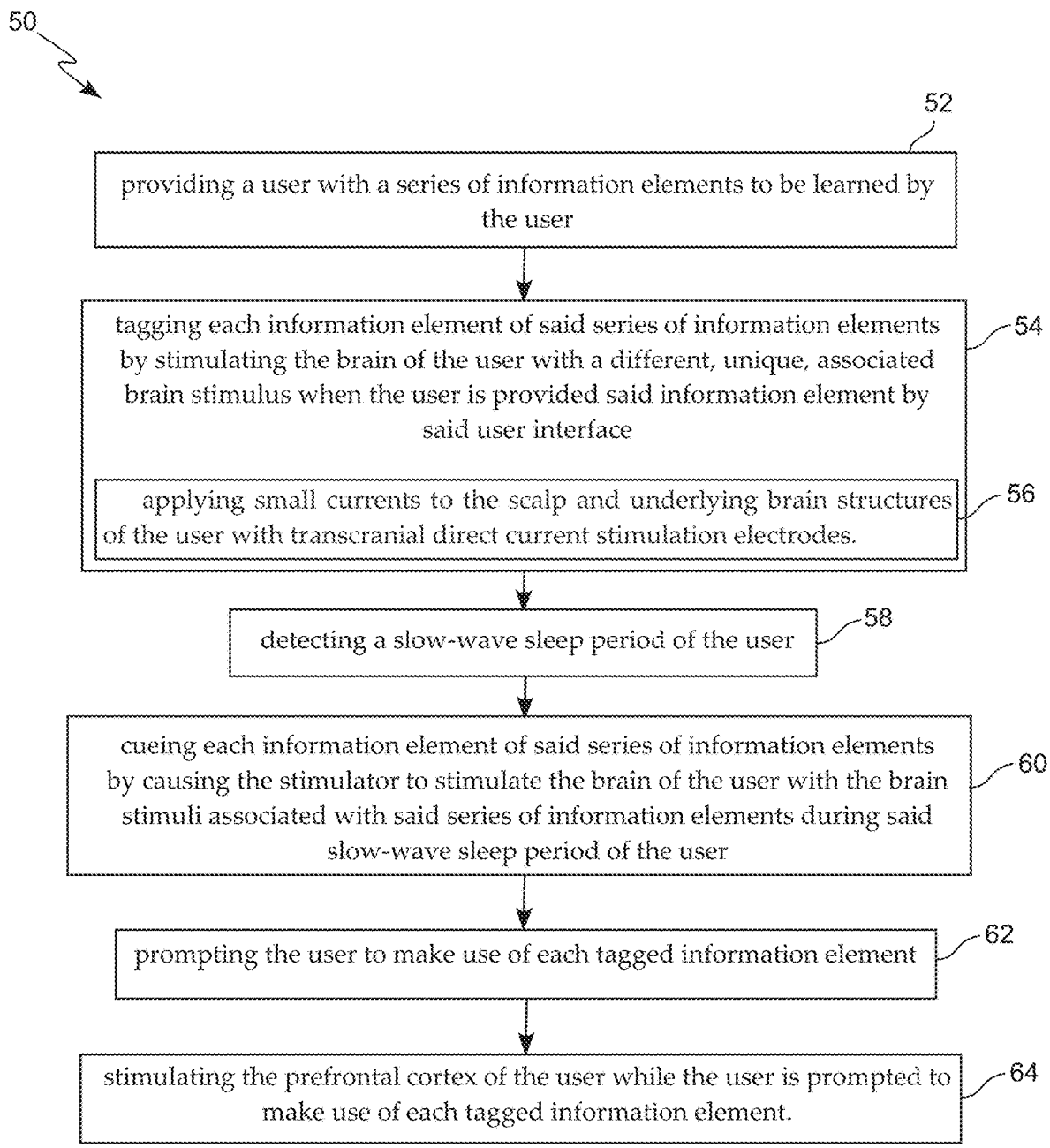
FIG. 6 illustrates a neuro stimulation method according to embodiments of this presentation.

FIG. 6 illustrates a neuro-stimulation method 50 according to embodiments of this presentation, the method comprising, with for example a user interface, providing 52 a user with a series of information elements to be learned by the user. According to embodiments of this presentation, the series of information elements to be learned by the user can comprise vocabulary lists, grammar rules, pronunciation exercises, or prosody examples, in a foreign language to be learned by the user.

According to embodiments of this presentation the method further comprises, with for example a non-invasive brain stimulator, tagging 54 each information element of said series of information elements. Said tagging can be accomplished by stimulating the brain of the user with a different, unique, associated brain stimulus when the user is provided said information element by said user interface. According to embodiments of this presentation, the stimulating of the brain of the user with the non-invasive stimulator can comprise applying 56 small currents to the scalp and underlying brain structures of the user with transcranial direct current stimulation electrodes.

According to embodiments of this presentation the method further comprises, with for example a non-invasive brain sensor, detecting 58 a slow-wave sleep period of the user. According to embodiments of this presentation the non-invasive brain sensor can comprise electroencephalogram sensor electrodes, and the detection of a slow wave sleep period can comprise the detection of electroencephalogram data evidencing a slow wave sleep period.

According to embodiments of this presentation the method further comprises cueing 60 each information element of the series of information elements by, during said slow-wave sleep period of the user, causing the stimulator to stimulate the brain of the user with the brain stimuli associated with said series of information elements.

According to embodiments of this presentation the method further comprises, with for example the user interface, prompting 62 the user to make use of each tagged information element; and with for example the non-invasive brain stimulator, stimulating 64 the prefrontal cortex of the user while the user is prompted to make use of each tagged information element.

The method can also further comprise updating a list of information that need be cued by: prompting the user to make use of each tagged information element; determining what tagged information element need to be cued during the sleep of the user and what tagged information element need not be cued during the sleep of the user (for example by logging behavioral performance of the user and/or determining what information elements have not been learned properly by the user, and what information elements have been learned properly by the user); and cueing only the information element that need to be cued.

Figure 7:
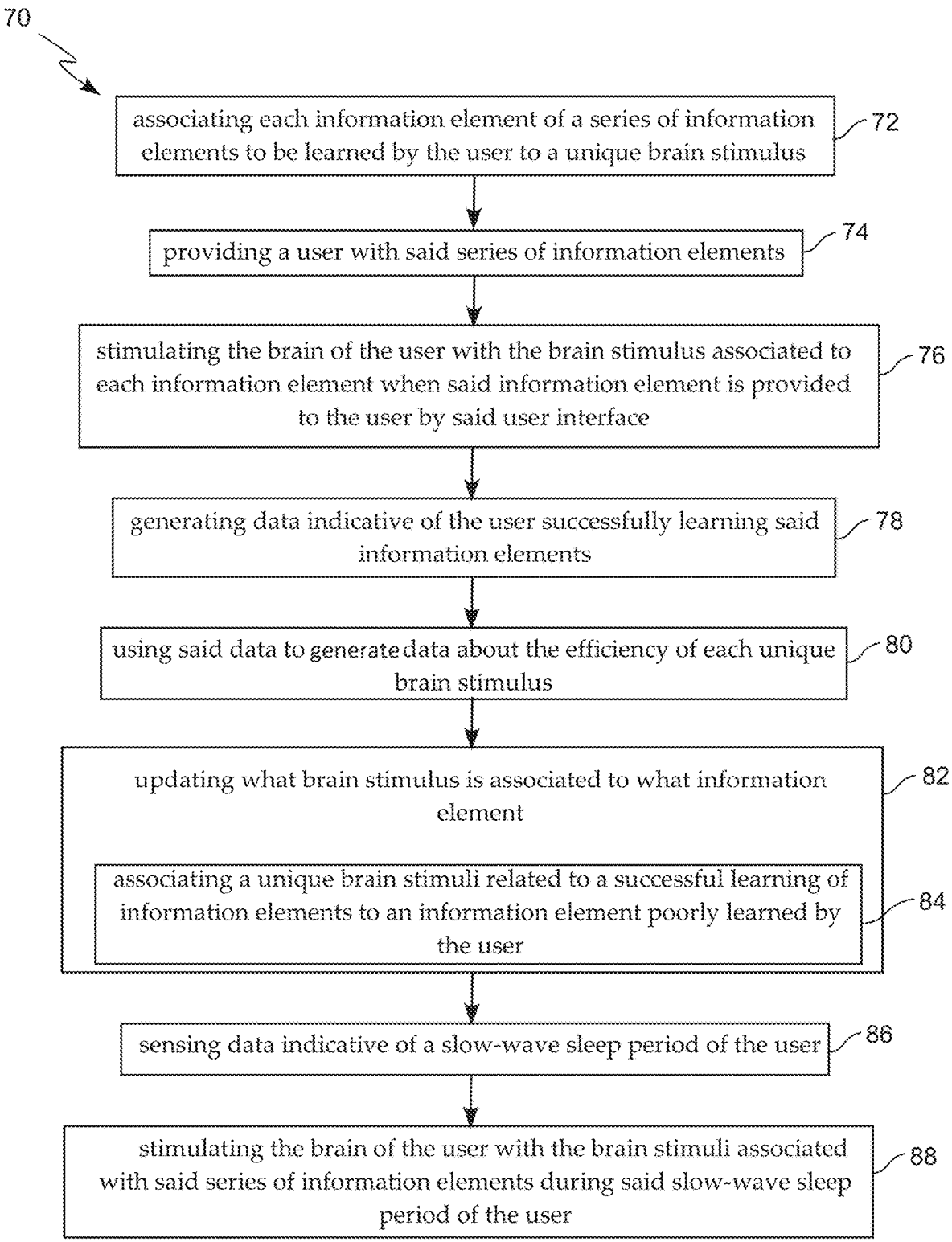
FIG. 7 illustrates a neuro stimulation method according to embodiments of this presentation.

FIG. 7 illustrates a neuro-stimulation method 70 according to embodiments of this presentation, the method comprising (with for example a curriculum and stimulation scheduler) associating 72 to a unique brain stimulus each information element of a series of information elements to be learned by a user. The brain stimuli can be picked from a library of existing brain stimuli or they can be generated on the spot, for example based on the material available for transmitting the brain stimuli to the user. According to an embodiment of this presentation the method further comprises, with for example a user sensory interface, providing 74 the user with said series of information elements; and with for example a user neural interface, stimulating 76 the brain of the user with the brain stimulus associated to each information element when said information element is provided to the user by said user interface.

According to an embodiment of this presentation the method further comprises, with for example the user sensory or neural interface, generating/outputting 78 data (sensory data or neural data) indicative of the user successfully learning the information elements; and with for example a predictive model, receiving and using 80 that data about what information elements are successfully learned to provide the curriculum and stimulation scheduler with data about the efficiency of each unique brain stimulus. According to an embodiment of this presentation the method further comprises, with for example the curriculum and stimulation scheduler, updating 82 what brain stimulus is associated to what information element, where said updating can include associating 84 a unique brain stimuli related to a successful learning of information elements to an information element poorly learned by the user.

According to an embodiment of this presentation the method further comprises, with for example the user neural interface, sensing 86 data indicative of a slow-wave sleep period of the user; and with for example the user neural interface, stimulating 88 the brain of the user with the brain stimuli associated with said series of information elements during said slow-wave sleep period of the user.

Systems designed at HRL Laboratories and disclosed for example in U.S. application Ser. No. 15/332,787, which is hereby incorporated by reference, allow targeting specific neural replays during slow wave sleep for stimulation, leading to improvement and acceleration of consolidation. By improving sleep and memory reactivation, one can decrease the incidence of MCI, which affects 15-20% of older adults and is associated with higher mortality rates.

Previous efforts in the field of neurostimulation have relied on manual stimulation without any specificity in time, which reduced the capabilities of the system, as well as the potential for the commercialization of this technology. By employing a closed-loop system that can automatically identify biomarkers for determining when to stimulate, the utility and capacity for commercialization of the system is increased. A system with closed-loop sensing and stimulation capability has been previously disclosed by HRL Laboratories' U.S. application Ser. No. 15/947,733, which is hereby incorporated by reference, and the current work can be considered as related to that technology.

Having now described the invention in accordance with the requirements of the patent statutes, those skilled in this art will understand how to make changes and modifications to the present invention to meet their specific requirements or conditions. Such changes and modifications may be made without departing from the scope and spirit of the invention as disclosed herein.

The foregoing Detailed Description of exemplary and preferred embodiments is presented for purposes of illustration and disclosure in accordance with the requirements of the law. It is not intended to be exhaustive nor to limit the invention to the precise form(s) described, but only to enable others skilled in the art to understand how the invention may be suited for a particular use or implementation. The possibility of modifications and variations will be apparent to practitioners skilled in the art. No limitation is intended by the description of exemplary embodiments which may have included tolerances, feature dimensions, specific operating conditions, engineering specifications, or the like, and which may vary between implementations or with changes to the state of the art, and no limitation should be implied therefrom.

Applicant has made this disclosure with respect to the current state of the art, but also contemplates advancements and that adaptations in the future may take into consideration of those advancements, namely in accordance with the then current state of the art. It is intended that the scope of the invention be defined by the Claims as written and equivalents as applicable. Reference to a claim element in the singular is not intended to mean "one and only one" unless explicitly so stated. Moreover, no element, component, nor method or process step in this disclosure is intended to be dedicated to the public regardless of whether the element, component, or step is explicitly recited in the Claims. No claim element herein is to be construed under the provisions of 35 U.S.C. Sec. 112, sixth paragraph, unless the element is expressly recited using the phrase "means for . . . " and no method or process step herein is to be construed under those provisions unless the step, or steps, are expressly recited using the phrase "comprising the step(s) of . . . ."

All elements, parts and steps described herein are preferably included. It is to be understood that any of these elements, parts and steps may be replaced by other elements, parts and steps or deleted altogether as will be obvious to those skilled in the art

What is claimed is:

1. A neuro-stimulation system comprising:
a curriculum and stimulation scheduler arranged for associating a different brain stimulus to each information element of a series of information elements to be learned by a user;
a user sensory interface arranged for providing the user with said series of information elements;
a user neural interface arranged for stimulating a brain of the user with the brain stimulus associated to each information element when said information element is provided to the user by said user sensory interface;
wherein at least one of the user sensory interface and the user neural interface is provided for outputting respectively sensory data indicative of the user successfully learning said information elements and neural data indicative of the user successfully learning said information elements;
the system further comprising a predictive model arranged for receiving at least one of said sensory and neural data, and for providing the curriculum and stimulation scheduler with data about an efficiency of each different brain stimulus;
the curriculum and stimulation scheduler being arranged for updating what brain stimulus is associated to what information element, said updating including associating a different brain stimuli related to a different successfully learned information element to each of a plurality of information elements poorly learned by the user.

2. The neuro-stimulation system of claim 1, wherein the user sensory interface comprises at least one of a keyboard, a screen, a microphone and a speaker.

3. The neuro-stimulation system of claim 1, wherein the user neural interface comprises a headgear having a plurality of electroencephalogram electrodes and a plurality of transcranial direct current stimulation electrodes.

4. The neuro-stimulation system of claim 1, wherein each different brain stimulus comprises a spatio-temporal, amplitude-modulated pattern of neural stimulation electrical signals.

5. The neuro-stimulation system of claim 1, wherein the user neural interface is arranged to sense data indicative of a slow-wave sleep period of the user; and wherein the user neural interface is arranged to stimulate the brain of the user with the brain stimuli associated with said series of information elements during said slow-wave sleep period of the user.

6. A neuro-stimulation method comprising:
with a curriculum and stimulation scheduler, associating a different brain stimulus to each information element of a series of information elements to be learned by a user;
with a user sensory interface, providing the user with said series of information elements;
with a user neural interface, stimulating a brain of the user with the different brain stimulus associated to each information element when said information element is provided to the user by said user sensory interface;
with at least one of the user sensory interface and the user neural interface, outputting respectively sensory data indicative of the user successfully learning said information elements and neural data indicative of the user successfully learning said information elements;
with a predictive model, receiving at least one of said sensory and neural data, and providing the curriculum and stimulation scheduler with data about the efficiency of each different brain stimulus; and
with the curriculum and stimulation scheduler, updating what brain stimulus is associated to what information element, said updating including associating a different brain stimuli related to a different successfully learned of information element to each of a plurality of information elements poorly learned by the user.

7. The neuro-stimulation method of claim 6, wherein said user sensory interface comprises at least one of a keyboard, a screen, a microphone and a speaker.

8. The neuro-stimulation method of claim 6, wherein said user neural interface comprises a headgear with a plurality of electroencephalogram electrodes and a plurality of transcranial direct current stimulation electrodes.

9. The neuro-stimulation method of claim 6, wherein each different brain stimulus comprises a spatio-temporal, amplitude-modulated pattern of neural stimulation electrical signals.

10. The neuro-stimulation method of claim 6 further comprising:
with the user neural interface, sensing data indicative of a slow-wave sleep period of the user; and
with the user neural interface, stimulating the brain of the user with the brain stimuli associated with said series of information elements during said slow-wave sleep period of the user.

11. The neuro-stimulation system of claim 1, wherein the series of information elements to be learned by the user comprises one of:
a series of words of a vocabulary lists in a foreign language to be learned by the user, each information element being a word of said series of words;
a series of grammar rules in a foreign language to be learned by the user, each information element being a grammar rule of said series of grammar rules;
a series of pronunciation exercises in a foreign language to be learned by the user, each information element being a pronunciation exercise of said series of pronunciation exercises; and
a series of prosody examples in a foreign language to be learned by the user, each information element being a prosody example of said series of prosody examples.

12. The neuro-stimulation method of claim 6, wherein the series of information elements to be learned by the user comprises one of:
a series of words of a vocabulary lists in a foreign language to be learned by the user, each information element being a word of said series of words;
a series of grammar rules in a foreign language to be learned by the user, each information element being a grammar rule of said series of grammar rules;
a series of pronunciation exercises in a foreign language to be learned by the user, each information element being a pronunciation exercise of said series of pronunciation exercises; and
a series of prosody examples in a foreign language to be learned by the user, each information element being a prosody example of said series of prosody examples.

\* \* \* \* \*